(12) United States Patent
Lo et al.

(10) Patent No.: US 6,803,341 B2
(45) Date of Patent: Oct. 12, 2004

(54) METHOD OF A HIGH STABILITY SELECTABLE HYDROGENATE CATALYST PRODUCING AND USING FOR DMCHD MANUFACTURING

(75) Inventors: Man-Yin Lo, Hsinchu (TW); Mei-Yuan Chang, Hsinchu (TW)

(73) Assignee: Chinese Petroleum Corporation, Taipei (TW)

( * ) Notice: Subject to any disclaimer, the term of this patent is extended or adjusted under 35 U.S.C. 154(b) by 82 days.

(21) Appl. No.: 10/050,818

(22) Filed: Jan. 18, 2002

(65) Prior Publication Data

US 2003/0153456 A1 Aug. 14, 2003

(51) Int. Cl.$^7$ .................................................. B01J 23/56
(52) U.S. Cl. .......................................................... 502/332
(58) Field of Search ........................................... 502/332

(56) References Cited

U.S. PATENT DOCUMENTS

| | | | | |
|---|---|---|---|---|
| 3,027,398 A | * | 3/1962 | Foohey | 560/127 |
| 3,444,237 A | * | 5/1969 | Jaffe | 560/127 |
| 5,286,898 A | * | 2/1994 | Gustafson et al. | 560/127 |
| 5,319,129 A | * | 6/1994 | Gustafson et al. | 560/127 |
| 5,399,742 A | * | 3/1995 | Tennant et al. | 560/127 |
| 6,018,048 A | * | 1/2000 | Morikawa et al. | 546/185 |
| 6,187,968 B1 | * | 2/2001 | Itoh et al. | 568/831 |
| 6,294,703 B1 | * | 9/2001 | Hara et al. | 568/831 |
| 6,545,120 B1 | * | 4/2003 | Ooga et al. | 528/275 |

OTHER PUBLICATIONS

US 20030144460A1.*
US 20030153456A1.*

* cited by examiner

*Primary Examiner*—Steven Bos
*Assistant Examiner*—William G Wright
(74) *Attorney, Agent, or Firm*—Rosenberg, Klein & Lee

(57) ABSTRACT

The present invention is provided a method of a high stability selectable hydrogenate catalyst producing and using for MCHD manufacturing. The present invention comprised a preparing procedure for Ru/Al$_2$O$_3$ catalyst including ` an activity raising procedure for said catalyst including and a DMCHD manufacturing process which said high stability catalyst is used for a selectable hydrogenating reaction.

3 Claims, 1 Drawing Sheet

METHOD OF A HIGH STABILITY SELECTABLE HYDROGENATE CATALYST PRODUCING AND USING FOR DMCHD MANUFACTURING

A method of a high stability selectable hydrogenate catalyst producing and using for DMCHD manufacturing

FIELD OF THE INVENTION

The present invention relates to a method of a high stability selectable hydrogenate catalyst producing and using for DMCHD manufacturing. When Dimethyl tetephthalate(DMT) with the selectable hydrogenate catalyst produced Dimethyl 1,4-cyclohexanedicarboxylate (DMCHD), said catalyst do not lost activate over 500 hours and maintain DMCHD production ratio over 90% in a long time. This develop of research about manufacture of DMCHD, relate to industry, could reduce most cost of production and elevate efficiency of economy.

BACKGROUND OF THE INVENTION

In U.S. Pat. No. 5,399,742 and U.S. Pat. No. 5,319,129 suggests that cyclohexanedimethanol (CHDM) used to produce condensation polymer and particular monomer of polyester in currently, more particularity, used to produce the poly 1,4-cycohighhexanedimethylene terephthalate (PCT), there is high performance and high incident value, and glycol modified PET(PETG). However, the dimethyl 1,4-cyclohexanedicarboxylate(DMCHD) is one of the intermediate products during the reaction when made CHDM, first we must synthetic DMCHD for production of CHDM. So there is very high value of economy to DMCHD, the way of industry commit the development of research.

So far, catalyst to synthetic DMCHD has two catalysts system one is Pd—$Al_2O_3$ the other is $Ru/Al_2O_3$. When used catalyst of $Pd/Al_2O_3$, it need more high pressure (10–200 bar) and more high temperature (140–400° C.). It is easy to infect by CO of sub-production. Although the more novelty catalyst of $Ru/Al_2O_3$ can react in more low pressure (10–175 bar) and more low temperatures 150–230° C.), without a matter of infection by CO of sub-production, and the fault of said catalyst so easy lost activation that employ too short about prescription and low production. The mainly reason of fault used mismanaged in activation condition so that too large particle of catalyst and distribution irregularity.

Table 7 gives conventional $Ru/Al_2O_3$ catalyst activation and reaction life, the conditions are pressure 700–750 psig, temperature 120° C., DMT 's space velocity 24 hour$^{-1}$. It is no obviously shifting but maintain high effectively 95%, DMT conversion ˋ DMCHD selectivity and DMCHD yield capacity, in reaction 5.3 hours. After 5.3 hours, DMT conversion ˋ DMCHD selectivity and DMCHD yield capacity is a large range decrease. After 240.1 hours, DMT conversion is 21.1%, DMCHD yield capacity is 16.47%, it is no tally for useful of industry and efficiency of economy. The DMCHD industry wanted to overcome that the fault of conventional $Ru/Al_2O_3$ catalyst is easier loss of activation.

SUMMARY OF THE PRESENT INVENTION

It is an object of the present invention to produce high stability for selectable hydrogenate catalyst having a catalyst to maintain long-term activation.

It is another object of the present invention to produce high stability for selectable hydrogenate catalyst having a activation method to produce a catalyst which used in synthetic DMCHD, the synthetic reaction process is in lower temperature and lower pressure. Thus, the catalyst is not easy loss activation and have long life of reaction, and maintain excellent stability and activation after long-term reaction. The industry is not reduce cost but also increase yield capacity, it is good for industry and relation industry.

It is another object of the present invention to produce high stability for selectable hydrogenate catalyst having a excellent reaction condition, convenient temperature ˋ pressure ˋ velocity of hydrogen gas ˋ space velocity of DMT material and concentration of DMT solution, react with said catalyst of selectable hydrogen reaction that could get 99% DMCHD yield capacity.

BRIEF DESCRIPTION OF THE DRAWINGS

A better understanding of the present invention will be obtained by reference to be detailed description below, in conjunction with the following drawing in which.

DETAILED DESCRIPTION OF THE PREFERRED EMBODIMENT

Figure 1:
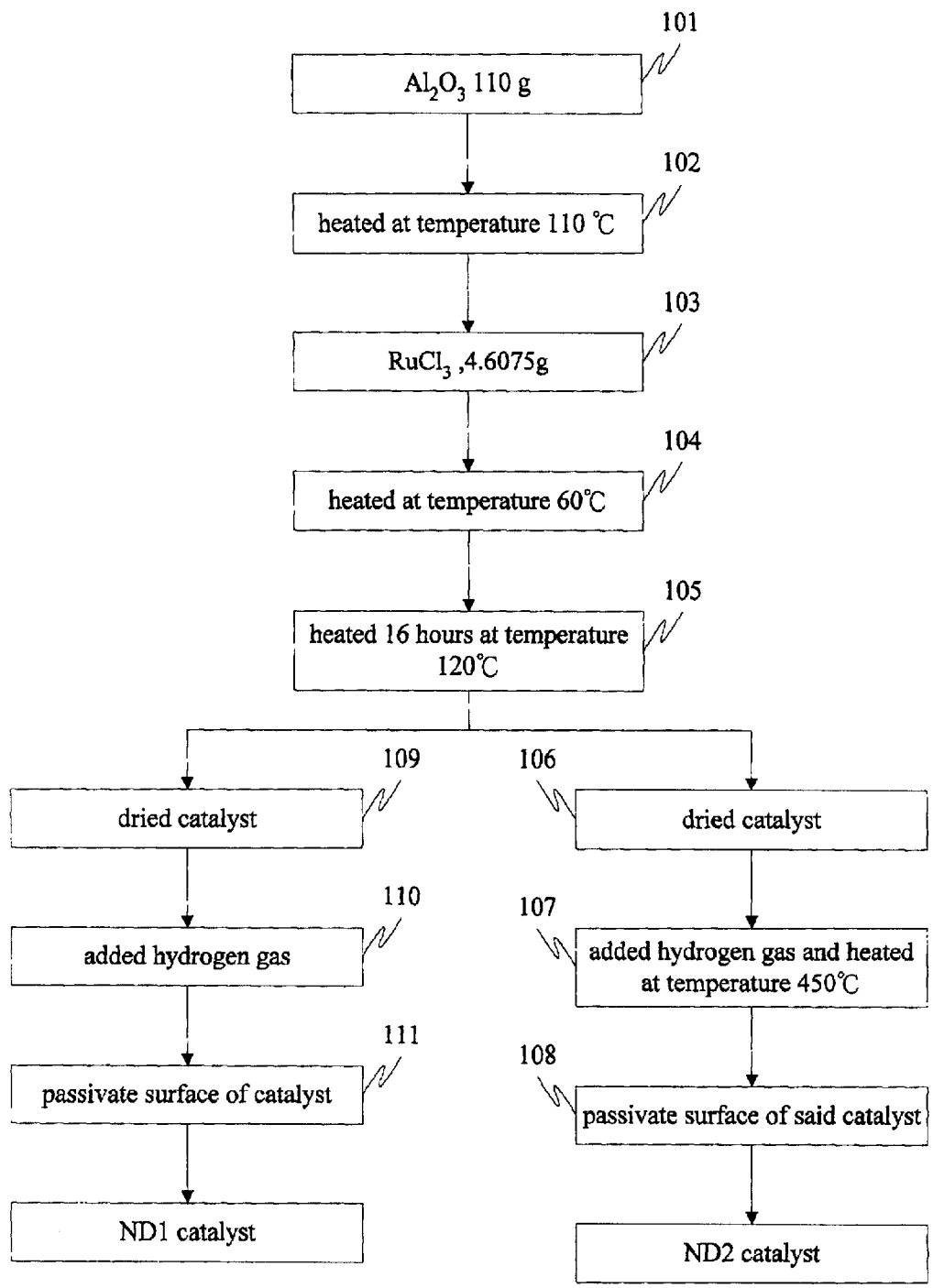
FIG. 1 is a illustration of an embodiment of the present invention.

While this present invention is satisfied by embodiments in a range of forms and methods, there will be described herein examples of the preferred embodiment of the invention, with the understanding that the present disclosure is to be considered as exemplary of the principles of the invention and is not intended to limit the invention to the embodiment described.

FIG. 1 illustrates the production process of conventional catalyst and present invention catalyst, first step 101 put Al2O3 110 grams into 500 ml cucurbit in vacuum; step 102 heated at temperature 110° C., after 6 hours stop heating, when cooled at atmospheric temperature stopped sprout vacuum; step 103 added $RuCl_3$ 4.6075 grams into cucurbit; step 104 heated at temperature 60° C. and made volatile solvent in vacuum; step 105 will produce catalyst heated 16 hours at temperature 120° C. in heater, cut catalyst one process this present invention of activation catalyst step the other process conventional activation catalyst step.

When process activation catalyst of this present invention, step 106 dried catalyst in steel breeder; step 107 added hydrogen gas and heated at temperature 450° C., after 2 hours stop heated; step 108, when cooled at atmospheric temperature added little air which passivate surface of said catalyst, finally produced ND2 catalyst (2% $Ru/Al_2O_3$).

When process conventional catalyst step used air as oxidant, step 109 will dried catalyst calcine in high temperature heater, until 12 hours at temperature 500° C. (10° C./min); step 110 added hydrogen gas in steel breeder of catalyst until heated 2 hours at temperature 450° C. stop heated; step 111 cooled atmospheric temperature added little air which passivate surface of catalyst, finally produced ND1 catalyst (2% $Ru/Al_2O_3$).

The results of present invention catalyst and conventional catalyst displayed better stability and activation in which reaction condition.

First, table 1 is a effectively DMCHD yield capacity of present invention catalyst hydrogenated with DMT at temperature and hydrogen gas velocity. The present invention catalyst hydrogenated with DMT, phenyl of DMT hydrogenated cyclohexane, generated product of DMCHD. The mainly DMT 3.5 wt. % used solvent of ethyl acetate which discussed yield capacity of DMCHD ˋ temperature and velocity of hydrogen gas at pressure 700~800 psig. The product used off-line GC analysis, GC column used style of Stabilwax Restek Comp., calculated conversion of DMT and selectivity of DMCHD.

According to experiment data, 3rd for temperature factor can get 99.71% conversion of DMT 99.36% selectivity of DMCHD product and 99.07% yield capacity of DMCHD in 40 ml/min velocity of hydrogen gas and at reaction temperature 100° C. When added to temperature 120° C., conversion of DMT is 99.51% ﹅ selectivity of DMCHD product is 98.63% and yield capacity of DMCHD is 98.15%.

Consequently, the experiment can get higher conversion of DMT ﹅ selectivity and yield capacity of DMCHD at temperature 100° C., which present invention catalyst can get excellent product at more lightly temperature (100° C.) and lower mole ratio of $H_2$/DMT(27.6). The more helpful decreased cost of production and saved mileage of hydrogen gas and energy-intensive.

When reacted at temperature 100° C. for factor velocity of $H_2$, hydrogen gas velocity decreased to 10 ml/min and 20 ml/min. And conversion of DMT decreased dividually to 88.58% and 93.46%, yield capacity of DMCHD decreased dividually to 87.63% and 92.60% which lower than conversion of DMT is 99.71% and yield capacity of DMCHD is 99.07% in 40 ml/min velocity of hydrogen gas. However, velocity hydrogen gas decreased dividually to 10 ml/min and 20 ml/min at 120° C. reaction temperature, conversion of DMT decreased dividually to 94.68% and 94.68% and yield capacity of DMCHD decreased dividually to 62.66% and 94.38% which lower than conversion of DMT is 99.51% and yield capacity of DMCHD is 98.15% at 40 ml/min velocity of hydrogen gas. Everywhere temperature at 100° C. or 120° C. at 40 ml/min velocity of hydrogen gas can get higher conversion of DMT and yield capacity of DMCHD than velocity of hydrogen gas is 10 ml/min or 20 ml/min.

Table 2 is a yield capacity effectively of DMCHD for present invention catalyst hydrogenated with DMT at temperature and hydrogen gas velocity. According to experiment data, controlled LHSV range of DMT is $12h^{-1}$ ﹅ $24h^{-1}$ ﹅ $36h^{-1}$ and $48h^{-1}$ when changed velocity of hydrogen gas, so maintained mole ratio of H2/DMT 27.6 at same time changed velocity of hydrogen gas. Conversion of DMT is dividually 99.41% 99.51% 99.56% and 98.50% and can maintained over 97.25% yield capacity of DMCHD.

Table 3 is a yield capacity effectively of DMCHD for present invention catalyst hydrogenated with DMT, ethyl acetate solvated 10% w.t. DMT solution at temperature 117° C.~141° C. of LHSV dividual $6h^{-1}$ and $12h^{-1}$. The range of test can get over 98% excellent yield capacity of DMCHD at temperature 117° C. Conversion of DMT is 98.93% and selectivity of DMCHD is 99.15%. The result of yield capacity over than 98% is similar to use 3.5% w.t. DMT at temperature 120° C. but can use lower mole ratio of $H_2$/DMT (15.5), so present invention catalyst can be suit 10% w.t. concentration solution of DMT.

The yield capacity effectively of DMCHD discussed about temperature and velocity of hydrogen gas in conventional catalyst hydrogenation.

Table 4 is a yield capacity effectively of DMCHD to velocity of hydrogen gas of conventional catalyst $Ru/Al_2O_3$ hydrogenation with DMT. According to experiment, reacted dividually at velocity of hydrogen gas 10 ml/min ﹅20 ml/min and 40 ml/min at temperature 120° C. The result conversion of DMT and selectivity and yield capacity of DMCHD lower than used present invention catalyst in table 1 at same condition. In table 4, the best result is at 40 ml/min velocity of hydrogen gas here-at conversion of DMT is 97.89% and selectivity of DMCHD product is 97.49% and yield capacity only have 95.43% lower than used present invention catalyst in table 1 at same condition. Obviously, present invention catalyst have elevated effectively of selectivity and yield capacity of DMCHD.

Table 5 is a yield capacity effectively of DMCHD to temperature of conventional catalyst $Ru/Al_2O_3$ hydrogenation with DMT. The result displayed that elevated temperature sequent elevated conversion of DMT form temperature 120° C. added to 97.89% to temperature 200° C. added to 99.58%. But selectivity of DMCHD decreased 97.49% to 93.66% form temperature 120° C. to 200° C. Reaction displayed not too high at temperature, when can get higher 95.79% yield capacity of DMCHD at temperature 140° C. lower than present invention catalyst reacted yield capacity of DMCHD at temperature 100° C. is 99.07% and at temperature 120° C. is 98.15%. Obviously, present invention catalyst can get higher yield capacity of DMCHD in lower temperature than conventional, present invention produced DMCHD not but saving energy also decreased cost of production.

For the purposed of understanding present invention more stability ﹅ high activation and difficulty lost activation than conventional, following is list relation property.

Table 6 is test about catalyst life of present invention catalyst hydrogenated with DMT, test in table 1, present invention catalyst hydrogenated with DMT in breeder, DMT (3.5 w.t. %) solvated with ethyl acetate, produced product of DMCHD under benzene-ring hydrogenation reaction at pressure 700~800 psig and temperature 120° C. controlled LHSV $12h^{-1}$ and $24h^{-1}$, velocity of hydrogen gas is 10 ml/min, mole ration to $H_2$/DMT is divitual 55.2 and 27.6, the product analyzed composition with GC and calculated conversion of DMT and selectivity of product.

The experiment data showed, after reaction 70 hours maintained 99% conversion of DMT and 99% selectivity of DMCHD no obviously change at $12h^{-1}$ LHSV, catalyst can lost activation. Conversion of DMT and selectivity of DMCHD decreased divitual to 92.10% and 97.78% when elevated to $24h^{-1}$ LHSV, the result attribution recant decreased complex time with catalyst and decreased mole ratio of H2/DMT from 55.2 to 27.6. When reaction continued to 572.5 hours, the experiment data displayed that catalyst could not lose activation and selectivity, non-obviously lost activation. So present invention catalyst have excellent stability, it is suit mass production in industry.

Table 7 is stability test about conventional catalyst activation process, controlled $24h^{-1}$ LHSV of DMT, after 5.30 hours non-obviously changed about conversion of DMT between 97.89% and 99.74% and selectivity of DMCHD between 96.94% and 97.81% which displayed no loss activation of catalyst. Conversion of DMT and selectivity of DMCHD decreased to 73.52% and 94.73% after reaction 76 hours. Conversion of DMT and selectivity of DMCHD decreased divitually to 21.20% and 78.06% which showed seriously loss activation, yield capacity is not accomplishment of mileage economy.

According table 6 and table 7 showed that present invention catalyst carried excellent stability adapted mass production in industry.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

TABLE 1

| No. | Temp (° C.) | velocity of H$_2$ (ml/min) | DMT LHSV (h$^{-1}$) | Conversion of DMT (%) | Selectivity of DMCHD (%) | Yield capacity of DMCHD (%) |
| --- | --- | --- | --- | --- | --- | --- |
| 1 | 100 | 10 | 24 | 88.58 | 98.92 | 87.63 |
| 2 | 100 | 20 | 24 | 93.46 | 99.09 | 92.60 |
| 3 | 100 | 40 | 24 | 99.71 | 99.36 | 99.07 |
| 4 | 120 | 10 | 24 | 94.68 | 97.86 | 92.66 |
| 5 | 120 | 20 | 24 | 96.30 | 98.00 | 94.38 |
| 6 | 120 | 40 | 24 | 99.51 | 98.63 | 98.15 |

TABLE 2

| No. | Temp (° C.) | velocity of H$_2$ (ml/min) | DMT LHSV (h$^{-1}$) | Conversion of DMT (%) | Selectivity of DMCHD (%) | Yield capacity of DMCHD (%) |
| --- | --- | --- | --- | --- | --- | --- |
| 1 | 120 | 20 | 12 | 99.41 | 98.79 | 98.20 |
| 2 | 120 | 40 | 24 | 99.51 | 98.63 | 98.15 |
| 3 | 120 | 60 | 36 | 99.56 | 98.77 | 98.34 |
| 4 | 120 | 80 | 48 | 98.50 | 98.73 | 97.25 |

TABLE 3

| No. | Temp (° C.) | velocity of H$_2$ (ml/min) | DMT LHSV (h$^{-1}$) | Conversion of DMT (%) | Selectivity of DMCHD (%) | Yield capacity of DMCHD (%) |
| --- | --- | --- | --- | --- | --- | --- |
| 1 | 140 | 50 | 6 | 99.53 | 99.29 | 98.82 |
| 2 | 141 | 50 | 12 | 99.64 | 98.88 | 98.52 |
| 3 | 117 | 50 | 12 | 98.93 | 99.15 | 98.09 |

TABLE 4

| No. | Temp (° C.) | velocity of H$_2$ (ml/min) | DMT LHSV (h$^{-1}$) | Conversion of DMT (%) | Selectivity of DMCHD (%) | Yield capacity of DMCHD (%) |
| --- | --- | --- | --- | --- | --- | --- |
| 1 | 120 | 10 | 24 | 79.42 | 95.31 | 75.70 |
| 2 | 120 | 20 | 24 | 89.71 | 97.06 | 85.07 |
| 3 | 120 | 40 | 24 | 97.89 | 97.49 | 95.43 |

TABLE 5

| No. | Temp (° C.) | velocity of H$_2$ (ml/min) | DMT LHSV (h$^{-1}$) | Conversion of DMT (%) | Selectivity of DMCHD (%) | Yield capacity of DMCHD (%) |
| --- | --- | --- | --- | --- | --- | --- |
| 1 | 120 | 40 | 24 | 97.89 | 97.49 | 95.43 |
| 2 | 140 | 40 | 24 | 98.03 | 97.72 | 95.79 |
| 3 | 160 | 40 | 24 | 99.54 | 96.18 | 95.73 |
| 4 | 180 | 40 | 24 | 99.58 | 93.66 | 93.27 |
| 5 | 200 | 40 | 24 | 99.58 | 93.66 | 93.27 |

TABLE 6

| No. | DMT LHSV (h$^{-1}$) | React. hour (hrs) | Conversion of DMT (%) | Selectivity of DMCHD (%) | Yield capacity of DMCHD (%) |
|---|---|---|---|---|---|
| 1 | 12 | 1 | 99.5 | 99.5 | 99.00 |
| 2 | 12 | 10 | 99.41 | 98.79 | 98.20 |
| 3 | 12 | 20 | 99.85 | 93.34 | 99.20 |
| 4 | 12 | 30 | 99.04 | 99.26 | 98.31 |
| 5 | 12 | 70 | 99.08 | 99.60 | 98.69 |
| 6 | 24 | 80 | 92.10 | 97.78 | 90.05 |
| 7 | 24 | 100 | 92.90 | 97.95 | 91.00 |
| 8 | 24 | 120 | 94.21 | 97.64 | 91.96 |
| 9 | 24 | 140 | 94.34 | 97.50 | 91.98 |
| 10 | 24 | 171 | 93.19 | 98.55 | 91.84 |
| 11 | 24 | 200 | 93.77 | 97.89 | 91.79 |
| 12 | 24 | 210 | 92.42 | 99.60 | 92.05 |
| 13 | 24 | 240 | 93.71 | 98.22 | 92.05 |
| 14 | 24 | 360.0 | 93.60 | 98.05 | 91.78 |
| 15 | 24 | 384.5 | 93.00 | 97.62 | 90.79 |
| 16 | 24 | 408.3 | 94.39 | 98.19 | 92.68 |
| 17 | 24 | 480.0 | 92.69 | 97.74 | 90.59 |
| 18 | 24 | 527.5 | 92.15 | 97.79 | 90.35 |

TABLE 7

| No. | React. hour (hrs) | Conversion of DMT (%) | Selectivity of DMCHD (%) | Yield capacity of DMCHD (%) |
|---|---|---|---|---|
| 1 | 0.4 | 99.74 | 96.94 | 96.69 |
| 2 | 3.15 | 98.76 | 97.52 | 96.31 |
| 3 | 5.30 | 97.89 | 97.49 | 95.43 |
| 4 | 76.00 | 73.52 | 94.73 | 69.64 |
| 5 | 148.60 | 72.95 | 94.72 | 69.10 |
| 6 | 169.75 | 68.58 | 93.76 | 64.30 |
| 7 | 240.1 | 21.10 | 78.06 | 16.47 |

What claimed is:

1. A method of preparing a high stability selective hydrogenation catalyst for use in DMCHD manufacturing including the steps of:
   forming an Ru/Al$_2$O$_3$ catalyst including:
   a. inserting 110 grams Al$_2$O$_3$ into a triple neck bottle under vacuum conditions;
   b. heating said bottle at a temperature of 110° C. for 6 hours;
   c. cooling to ambient temperature then removing the bottle from vacuum conditions;
   d. adding a solution of 4.6 grams RuCl$_3$ into said bottle and heating at a temperature of 60° C.;
   e. drying said solution by vacuum suction; and
   f. heat heating said bottle in a heater at a temperature of 120° C. for 16 hours; whereby the catalyst activity is raised by the steps of:
   g. removing the intermediate product of Ru/Al$_2$O$_3$ catalyst from said bottle after step f, and putting said intermediate product into a stainless steel breeder;
   h. adding hydrogen gas into said breeder at a predetermined flow rate and heating at a temperature of 450° C. for 2 hours; and
   i. cooling to atmospheric temperature and then adding a small quantity of air for passivating the surface of said catalyst to obtain a high stability catalyst for selective hydrogenation in a DMCHD manufacturing process.

2. A method for producing high stability selective hydrogenation catalyst according to steps a–f of claim 1, wherein said Al$_2$O$_3$ and RuCl$_3$ has a fixed ratio of 110:4.6075 by wt.

3. A method for producing high stability selective hydrogenation catalyst according to step h of claim 1, wherein said predetermined flow rate of hydrogenate gas is 10 to 40 ml/mm.

* * * * *